US00PP29700P3

(12) United States Plant Patent
Olesen

(10) Patent No.: US PP29,700 P3
(45) Date of Patent: Sep. 25, 2018

(54) MINIATURE ROSE PLANT NAMED 'POULPAH084'

(50) Latin Name: ***Rosa* hybrid**
Varietal Denomination: Poulpah084

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/330,291

(22) Filed: Sep. 6, 2016

(65) Prior Publication Data

US 2018/0070500 P1 Mar. 8, 2018

(51) Int. Cl.
*A01H 5/02* (2018.01)

(52) U.S. Cl.
USPC ..... Plt./119
CPC ..... *A01H 5/0222* (2013.01)

(58) Field of Classification Search
USPC ..... Plt./101, 116, 119
See application file for complete search history.

(56) References Cited

PUBLICATIONS

PLUTO: Plant Variety Database, Oct. 20, 2017, citation for Poulpah084. 1 page.*
Floradania.dk website. 2015. http://floradania.dk/fileadmin/s3/pdf/nyhedskatalog/2015/News_-_Neuheiten_2015.pdf. Accessed Oct. 20, 2017. 1 page.*

* cited by examiner

*Primary Examiner* — Susan McCormick Ewoldt
*Assistant Examiner* — Karen M Redden

(57) ABSTRACT

A new garden rose plant of the Miniature class which has abundant, orange blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah084'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpah084', originated as a single seedling from the stated cross.

The new variety may be distinguished from its male pollen parent and female seed parent primarily by the following characteristics. The male pollen parent plant has near white flowers, while the new variety has orange blend flower color. The female seed parent plant has yellow flowers, while the new variety has orange blend flower color.

The objective of the hybridization of this rose variety was to create a new and distinct variety for garden use with unique qualities, such as:

1. Uniform and abundant orange blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah084' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpah084' was selected in the spring of 2011 by the inventor as a single plant from the progeny of the aforementioned hybridization.

Asexual reproduction of 'Poulpah084' by traditional budding and rooted cuttings was first done by Mogens N. Olesen in the nursery in Fredensborg, Denmark in July, 2011. This initial and other subsequent asexual propagations conducted in controlled environments have demonstrated that the characteristics of 'Poulpah084' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah084'.

Specifically illustrated in FIG. 1 of the drawings are flowers at various stages of development, petals detached, reproductive flower parts, and sepals detached.

Figure 1:
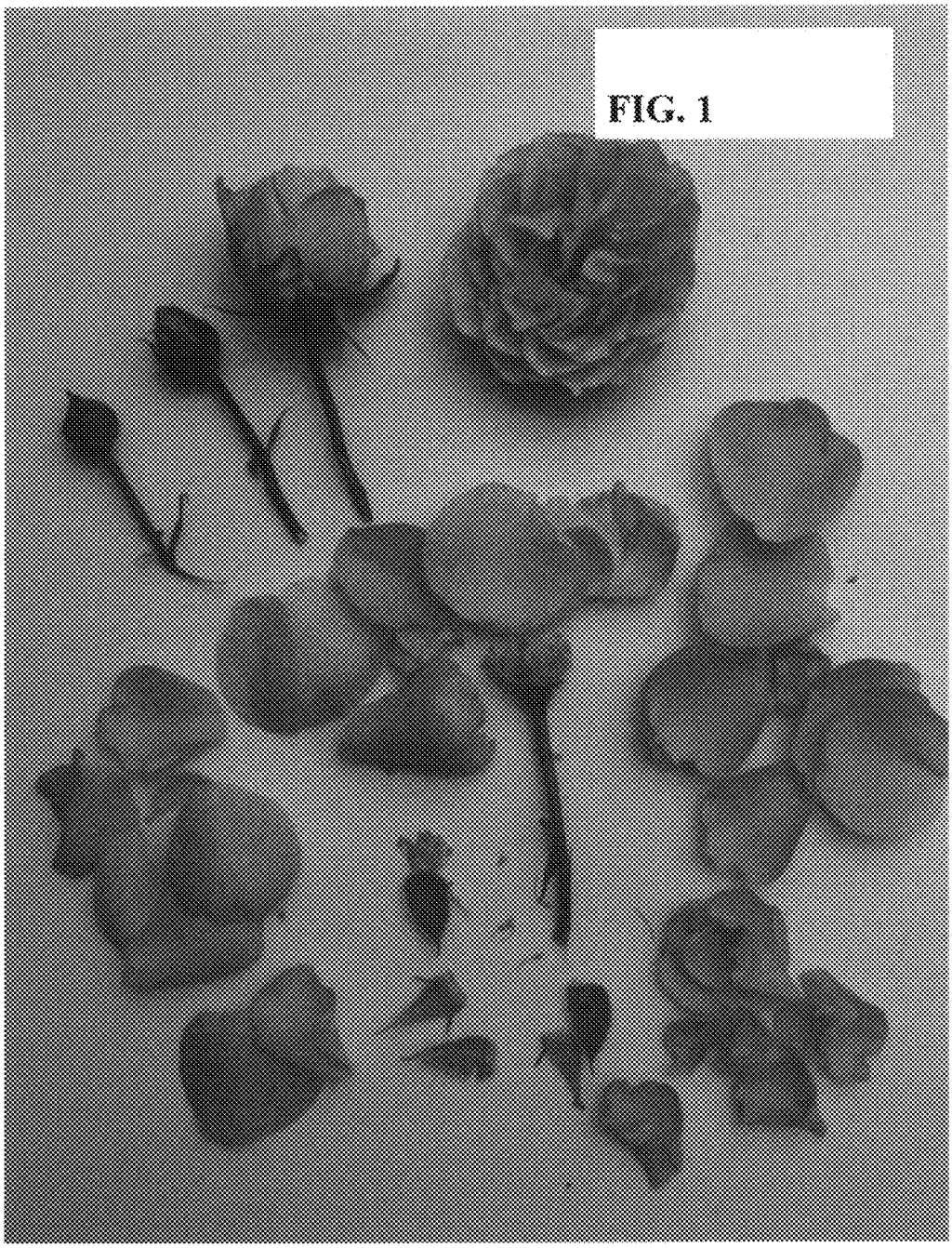
Figure 2:
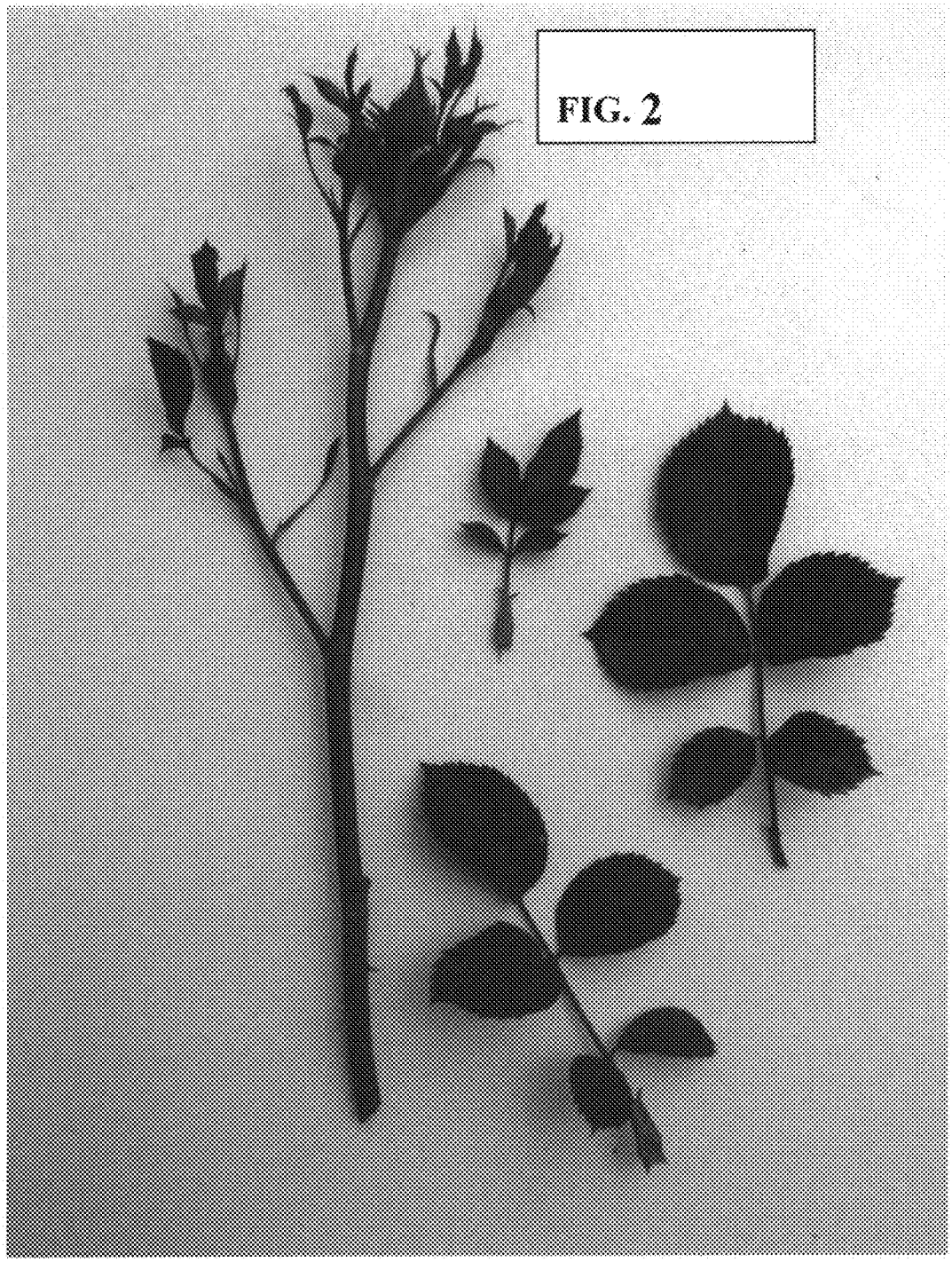

Shown in FIG. 2 are leaves, bare stem, and flowering stem showing attachment of peduncles. Plants shown are 2 years of age.

DETAILED DESCRIPTION OF THE VARIETY

The following is a description of 'Poulpah084', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulbambe', U.S. Plant Pat. No. 13,292 are compared to 'Poulpah084' in Chart 1.

CHART 1

| | 'Poulpah084' | 'Poulbambe' |
|---|---|---|
| Petal Count | 45 | 18-22 |
| Flower Diameter | 60 mm | 60 mm |
| General Tonality of Flower Color | Yellow-Orange Group 18B blended with Yellow-Orange Group 21C | Yellow-Orange Group 19A |

FLOWER AND FLOWER BUD

Blooming habit: Continuous.

Flower bud:

*Size.*—Upon opening, 18 mm in length from base of receptacle to end of bud. Bud diameter is 16 mm.

*Bud form.*—Ovoid.

*Bud color.*—As sepals divide petals are Yellow-Orange Group 16B with intonations of Orange-Red Group N34B and Yellow-Orange Group 15A.

*Sepal inner surface.*—Color: Yellow-Green Group 145C. Surface: Lightly pubescent.

*Sepal outer surface.*—Color: Yellow-Green Group 144A with light intonations of Greyed-Purple Group 183B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—25 mm long, 10 mm wide.

*Receptacle.*—Texture: Smooth. Size: 7 mm in height, 10 mm wide. Color: Yellow-Green Group 144A. Shape: Funnel.

*Pedicel.*—Surface: Smooth. Length: 25 to 30 mm. Diameter: 3 mm on average. Color: Yellow-Green Group 144A with intonations of Greyed-Purple Group 183B. Strength: Strong.

*Peduncle.*—Length: 3 to 6 cm. Diameter: About 4 mm. Color: Yellow-Green Group 145A. Texture: Smooth.

Flower bud development: Flower buds are borne in clusters of 3 to 5 flower buds per stem.

Flower bloom:

*Fragrance.*—Moderate perfume.

*Duration.*—The blooms have a duration on the plant of approximately 15 days. Petals fall cleanly away from plant after flowers have fully matured.

*Size.*—Flower diameter is 60 mm when open. Flower depth is 35 mm.

*Flower shape.*—Rosette, double, with many slightly overlapping petals of different sizes.

Petalage: Under normal conditions, flowers have 45 petals total, 3 of which are petaloids.

General tonality of flower: Open flowers are Yellow-Orange Group 18B blended with Yellow-Orange Group 21C.

Petal color:

*Upon opening, outer petals.*—Upper surface: Yellow-Orange Group 18B blended with intonations of Red Group 38C. At the basal zone petals are Yellow Group 12B. Lower surface: Orange Group 27C with intonations of Red Group 38A. At the basal zone petals are Yellow Group 12C.

*Upon opening, inner petals.*—Upper surface: Mainly Yellow-Orange Group 16B, becoming Yellow Group 12A at the base. Lower surface: Yellow-Orange Group 20B splashed with Orange Group 29B. Becoming Yellow Group 10B at the basal zone.

Petals:

*Petal reflex.*—Flat.

*Margin.*—Moderate to strong undulations with occasional cleft.

*Shape.*—Broad and rounded. Apex shape: Rounded. Base shape: Rounded.

*Size.*—40 mm (l)×45 mm (w).

*Texture.*—Smooth.

*Thickness.*—Average.

Petaloids:

*Size.*—20 mm (l) by 12 mm (w).

*Quantity.*—About 8.

*Shape.*—Irregular, with an acute base and rounded apex.

*Color.*—Upper side, Yellow-Orange Group 16B, becoming Yellow Group 12A at base. Lower side, Yellow-Orange Group 20B splashed with Orange Group 29B. Becoming Yellow Group 10B at the basal zone.

Reproductive flower parts:

*Pollen.*—None observed.

*Anthers.*—Size: 1 mm in length. Color: Greyed-Orange Group 167B. Quantity: 25 on average.

*Filaments.*—Color: Yellow Group 12A. Length: 5 mm.

*Pistils.*—Length: 3 mm. Quantity: 20 on average.

*Stigmas.*—Color: Yellow-Green Group 145D.

*Styles.*—Color: Yellow-Green Group 145D.

*Location of stigmas.*—Level in location relative to the length of the filaments and the height of the anthers.

*Hips.*—None Observed.

PLANT

Plant growth: Upright, bushy. Plants are 40 cm in height, and 30 cm wide.

Stems:

*Color.*—Juvenile growth: Yellow-Green Group 144B with intonations of Greyed-Orange Group 174A. Mature growth: Yellow-Green Group 144A.

*Length.*—On average, canes are 20 cm from the base of the plant to the flowering portion.

*Diameter.*—5 mm.

*Internodes.*—On mature canes about 30 mm between nodes.

*Surface texture.*—Young wood: Smooth. Older wood: Smooth.

Long prickles:

*Incidence.*—2 to 3 prickles per 10 cm of stem.

*Size.*—Average length of prickles on mature stems is 5 mm.

*Shape.*—Upper portion is linear. Lower portion is concave.

*Color.*—Juvenile prickles: Greyed-Red Group 179A. Mature prickles: Greyed-Orange Group 171C.

Plant foliage:

*Compound leaf.*—110 mm (l)×70 mm (w).

*Quantity.*—3 leaves per 10 cm of stem on average.

*Leaf bearing angle to the stem.*—45 degrees.

*Color of juvenile foliage*.—Upper side: Yellow-Green Group 144A with Greyed-Orange Group 166A. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 7 mm long, 2 mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 2 mm.

*Upper surface*.—Color: Yellow-Green Group 144A.

*Lower surface*.—Color: Yellow-Green Group 144B.

*Rachis*.—Length: 40 mm. Upper surface: Color: Yellow-Green Group 144A.

*Lower surface*.—Yellow-Green Group 144B. Color.

*Leaflet*.—Quantity: Normally 5 leaflets. Margins: Serrated. Size: On average terminal leaflets are 42 mm long, 32 mm wide. Shape: Generally elliptical. Base: Rounded. Apex: Cuspidate.

*Texture*.—Smooth.

*Thickness*.—Average.

*Arrangement*.—Odd pinnate.

*Venation*.—Reticulate.

*Glossiness*.—Moderately glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah084', substantially as illustrated and described herein, due to its abundant orange blend flowers, disease resistance, and extended period of bloom.

* * * * *